US012682520B2

(12) United States Patent　　　　　　(10) Patent No.:　US 12,682,520 B2
Gadgil et al.　　　　　　　　　　　　(45) Date of Patent:　　　Jul. 14, 2026

(54) MEDICAL DEVICES AND METHODS FOR PRESENTING CARDIAC INFORMATION FOR A PATIENT

(71) Applicant: GE Precision Healthcare LLC, Waukesha, WI (US)

(72) Inventors: Shruti Gadgil, Bangalore (IN); Dan Li, Shanghi (CN); Menglu Jiang, Shanghai (CN); Hui Hui, Wuxi (CN)

(73) Assignee: GE Precision Healthcare LLC, Waukesha, WI (US)

( * ) Notice: Subject to any disclaimer, the term of this patent is extended or adjusted under 35 U.S.C. 154(b) by 224 days.

(21) Appl. No.: 18/694,160

(22) PCT Filed: Oct. 11, 2021

(86) PCT No.: PCT/CN2021/123103
　　　§ 371 (c)(1),
　　　(2) Date: Mar. 21, 2024

(87) PCT Pub. No.: WO2023/060397
　　　PCT Pub. Date: Apr. 20, 2023

(65) Prior Publication Data
　　　US 2024/0285214 A1　　Aug. 29, 2024

(51) Int. Cl.
　　*G06T 11/26*　　　　(2026.01)
　　*G06T 11/10*　　　　(2026.01)
　　*A61B 5/339*　　　　(2021.01)

(52) U.S. Cl.
　　CPC .............. *G06T 11/26* (2026.01); *G06T 11/10* (2026.01); *A61B 5/339* (2021.01); *G06T 2210/41* (2013.01)

(58) Field of Classification Search
　　CPC . G06T 11/001; G06T 11/206; G06T 2210/41; A61B 5/339
　　See application file for complete search history.

(56) References Cited

U.S. PATENT DOCUMENTS

| 7,266,408 B2 | 9/2007 | Bojovic |
| 9,462,955 B2 | 10/2016 | Zhou |

(Continued)

FOREIGN PATENT DOCUMENTS

| CN | 1638692 | A | 7/2005 |
| CN | 102802517 | A | 11/2012 |
| EP | 1725165 | B1 | 12/2012 |

OTHER PUBLICATIONS

Meek, Steve et al., "ABC of clinical electrocardiography", British Medical Journal, vol. 324, Feb. 16, 2002, p. 415-418. (Year: 2002).*

(Continued)

*Primary Examiner* — Michelle L Sams

(57)　　　　　ABSTRACT

A method for presenting cardiac information originating from multiple leads connected to a patient. The method includes receiving the cardiac information collected via the multiple leads and detecting segment within the cardiac information. The method further includes creating a radar chart divided into sectors and plotting data points on the radar chart that correspond to the cardiac information for first and second sets of leads within the multiple leads, where the data points corresponding to the first set of leads are shown differently than the data points corresponding to the second set of leads so as to be visually distinguishable from each other.

17 Claims, 11 Drawing Sheets

(56)  References Cited

U.S. PATENT DOCUMENTS

| | | | | |
|---|---|---|---|---|
| 10,426,368 | B2 * | 10/2019 | Wang ..................... | A61B 5/339 |
| 2003/0097056 | A1 * | 5/2003 | Suzuki ................... | A61B 5/243 |
| | | | | 600/409 |
| 2005/0182333 | A1 * | 8/2005 | Nagata .................. | G06T 11/206 |
| | | | | 600/509 |
| 2009/0141593 | A1 * | 6/2009 | Taha ........................ | G01D 7/02 |
| | | | | 368/10 |
| 2011/0125042 | A1 * | 5/2011 | Xue ........................ | A61B 5/349 |
| | | | | 600/523 |
| 2011/0166469 | A1 | 7/2011 | Nagata | |
| 2013/0023780 | A1 * | 1/2013 | Cardinale .............. | A61B 5/339 |
| | | | | 600/523 |
| 2013/0131465 | A1 * | 5/2013 | Yamamoto ........... | A61B 5/7271 |
| | | | | 600/300 |
| 2014/0039338 | A1 * | 2/2014 | Nelwan .................. | A61B 5/339 |
| | | | | 600/523 |
| 2017/0156619 | A1 | 6/2017 | Couderc | |
| 2023/0120861 | A1 * | 4/2023 | Choudhuri .............. | G06F 40/40 |
| | | | | 705/2 |
| 2023/0147888 | A1 * | 5/2023 | Toth ..................... | A61B 5/0006 |
| | | | | 345/440 |

OTHER PUBLICATIONS

Excel Dashboards Template, "How-to Highlight or Color Rings in an Excel Radar Chart", Feb. 10, 2018, https://web.archive.org/web/20180210210816/http://www.exceldashboardtemplates.com/how-to-highlight-rings-or-color-rings-in-an-excel-radar-chart/ (Year: 2018).*
International Application No. PCT/CN2021/123103 filed Oct. 11, 2021—International Search Report and Written Opinion issued on May 30, 2022; 11 pages.
EP application 21960148.1 filed Mar. 19, 2024—extended Search Report issued Feb. 17, 2025; 9 pages.

* cited by examiner

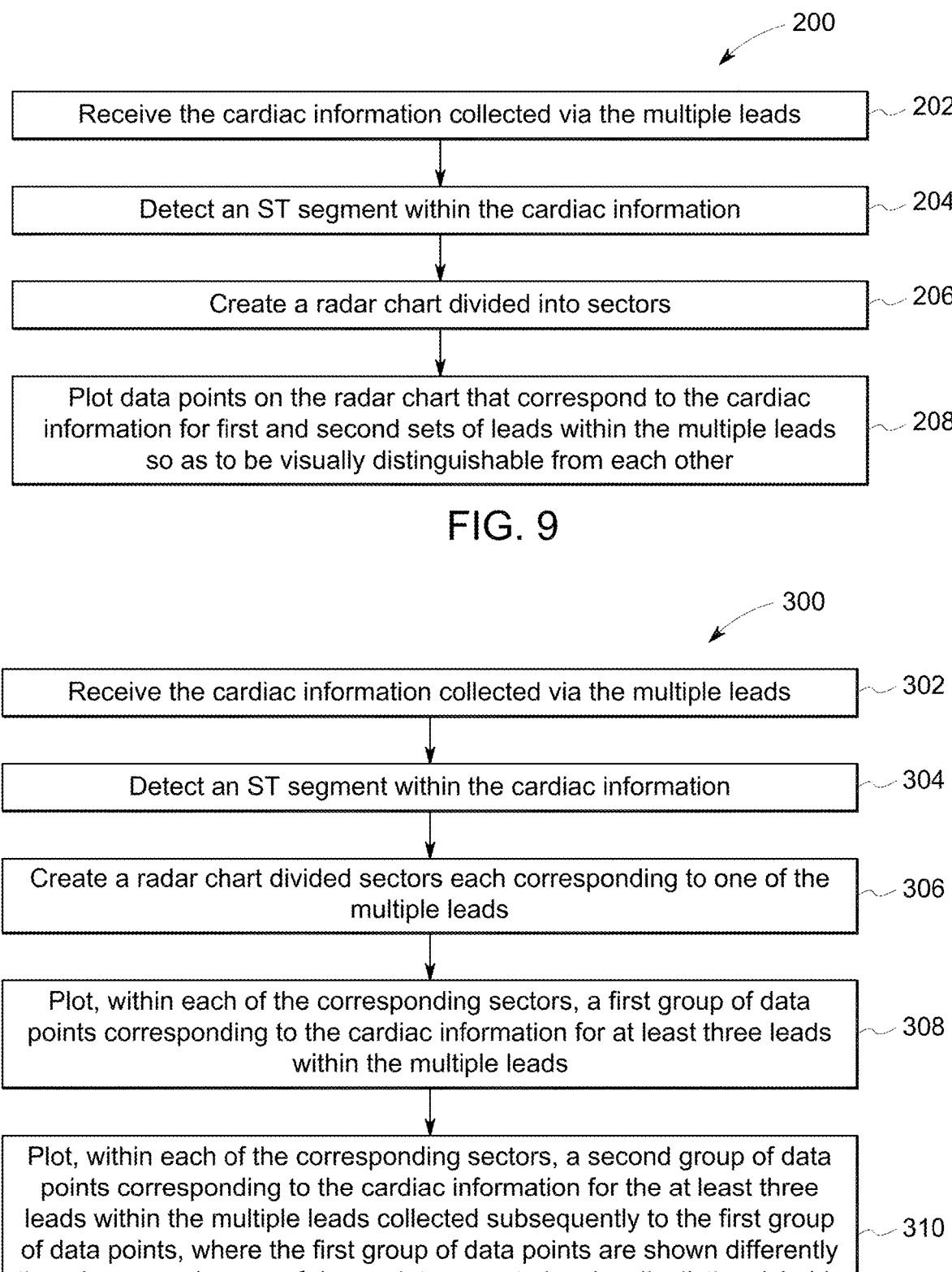

200

Receive the cardiac information collected via the multiple leads — 202

Detect an ST segment within the cardiac information — 204

Create a radar chart divided into sectors — 206

Plot data points on the radar chart that correspond to the cardiac information for first and second sets of leads within the multiple leads so as to be visually distinguishable from each other — 208

Receive the cardiac information collected via the multiple leads — 302

Detect an ST segment within the cardiac information — 304

Create a radar chart divided sectors each corresponding to one of the multiple leads — 306

Plot, within each of the corresponding sectors, a first group of data points corresponding to the cardiac information for at least three leads within the multiple leads — 308

Plot, within each of the corresponding sectors, a second group of data points corresponding to the cardiac information for the at least three leads within the multiple leads collected subsequently to the first group of data points, where the first group of data points are shown differently than the second group of data points so as to be visually distinguishable from each other — 310

FIG. 10

MEDICAL DEVICES AND METHODS FOR PRESENTING CARDIAC INFORMATION FOR A PATIENT

FIELD

The present disclosure generally relates to medical devices and methods for presenting cardiac information for a patient.

BACKGROUND

Patient monitors are essential medical devices, such as within a hospital environment. These and other medical devices generate time series data that a caregiver can monitor in real-time, and/or review at a later date. The time series data may include physiological data corresponding to a patient connected to the medical device, and/or other data relating to the functionality of the medical device itself, for example. Existing platforms for patient monitors include GE Healthcare's® B1×5 M/P platform.

Electrocardiography medical devices are one type of patient monitoring device routinely used, which are used to acquire data and generate electrocardiographs of a patient's heart activity (also referred to as an ECG). Caregivers routinely use ECGs to diagnose and treat cardiovascular issues in patients, often via 12 connections (also referred to as leads) to the patient used to measure voltages in the heart and voltage differentials across different leads and regions. The "ST" segment of an ECG waveform is particularly insightful for caregivers, which can be used to determine which particular region of the heart is likely experiencing issues, for example ischemia.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

One example of the present disclosure generally relates to a method for presenting cardiac information originating from multiple leads connected to a patient. The method includes receiving the cardiac information collected via the multiple leads and detecting a segment within the cardiac information. The method further includes creating a radar chart divided into sectors and plotting data points on the radar chart that correspond to the cardiac information for first and second sets of leads within the multiple leads, where the data points corresponding to the first set of leads are shown differently than the data points corresponding to the second set of leads so as to be visually distinguishable from each other.

In certain examples, each of the sectors corresponds to a different one of the multiple leads.

In certain examples, the first set of leads is associated with a first region of a heart and the second set of leads is associated with a second region of the heart. In further examples, the first region and the second region are distinct and are each one of an anterior region, an inferior region, and a lateral region, and where the first and second sets of leads each include between three and four of the multiple leads.

In certain examples, a first color of the data points for the first set of leads is different than a second color of the data points for the second set of leads. In further examples, the first color is the same for all of the data points within the first set of leads.

Certain examples of methods further include comparing values of the data points to one or more predetermined thresholds and automatically providing a visual indication when one of the data points exceeds the one or more predetermined thresholds.

Certain examples of methods further include plotting the data points on the radar chart that correspond to the cardiac information for a third set of leads within the multiple leads, where the data points corresponding to the third set of leads are shown differently than the data points corresponding to the first and second sets of leads so as to be visually distinguishable therefrom, and further include connecting the data points that are adjacent to each other within each of the first set of leads, the second set of leads, and the third set of leads, respectively, to form three overlapping shapes, respectively, where each of the three overlapping shapes has a different color.

In certain examples, the sectors each correspond to a period of time and the data points are plotted for the first and second sets of leads as a function of the period of time in which each was collected. In further examples, the first set of leads in a single lead among the multiple leads. Further examples include configuring the radar chart such that the period of time for each of the sectors based on a selection, and further include subsequently updating the data points plotted on the radar chart based on the selection. In further examples, the radar chart corresponds to a first region of the heart, and wherein all of the data points plotted on the radar chart correspond to individual leads among the multiple leads associated with the first region. In further examples, the data points are plotted continuously and in a circular manner around the radar chart such that older data points among the data points are overwritten by newer data points plotted after the older data points based on the period of time corresponding to the sectors. In further examples, a first color of the data points for the first set of leads is different than a second color of the data points for the second set of leads.

Certain examples of methods further include receiving one of at least a lead-based selection and a time-based selection, where receiving the lead-based selection causes the radar chart to be created such that each of the sectors corresponds to one of the multiple leads, and wherein receiving the time-based selection causes the radar chart to be created such that each of the sectors corresponds a period of time, and further includes subsequently updating the data points plotted on the radar chart based on which of the one of at least the lead-based selection and the time-based selection is received.

Another example of a method according to the present disclosure includes receiving the cardiac information collected via the multiple leads and detecting a segment within the cardiac information. The method further includes creating a radar chart divided sectors, where each of the sectors corresponds to one of the multiple leads, plotting, within each of the corresponding sectors, a first group of data points corresponding to the cardiac information for at least three leads within the multiple leads, and plotting, within each of the corresponding sectors, a second group of data points corresponding to the cardiac information for the at least three leads within the multiple leads collected subsequently to the first group of data points. The first group of data points are shown differently than the second group of data points so as to be visually distinguishable from each other. The method further includes determining differences between the second group of data points to the first group of data points for the multiple leads, comparing the differences to a threshold, and generating and transmitting an alert to an external device when at least one of the differences exceeds the threshold.

In certain examples, the second group of data points is shown to be darker than the first set of data points. Further examples include plotting an additional group of data points corresponding to the cardiac information for the at least three leads, wherein the first group of data points is removed from the radar chart, the second group of data points becomes the first group of data points, and the additional group of data points become the second group of data points.

Another example method according to the present disclosure includes receiving the cardiac information collected via the multiple leads, where the cardiac information comprises values collected from the multiple leads, and detecting a segment within the cardiac information. The method further includes creating a visual representation of a heart and depicting the heart having multiple regions, wherein each of the multiple leads is associated with one of the multiple regions of the heart. The method further includes presenting the values of the cardiac information for at least three leads within the multiple leads so as to be visually associated with each of the multiple regions corresponding thereto.

Certain examples of methods further include depicting a first region within the multiple regions as a different color than a second region within the multiple regions, and further comprising comparing the values to one or more predetermined thresholds and automatically providing a visual indication when one of the values exceeds the one or more predetermined thresholds.

Various other features, objects and advantages of the disclosure will be made apparent from the following description taken together with the drawings.

BRIEF DESCRIPTION OF THE DRAWINGS

The present disclosure is described with reference to the following drawings.

FIG. 9 is a flow chart for a first example of a method for presenting cardiac information according to the present disclosure;

FIG. 10 is a flow chart for a second example of a method for presenting cardiac information according to the present disclosure;

DETAILED DISCLOSURE

Figure 1:
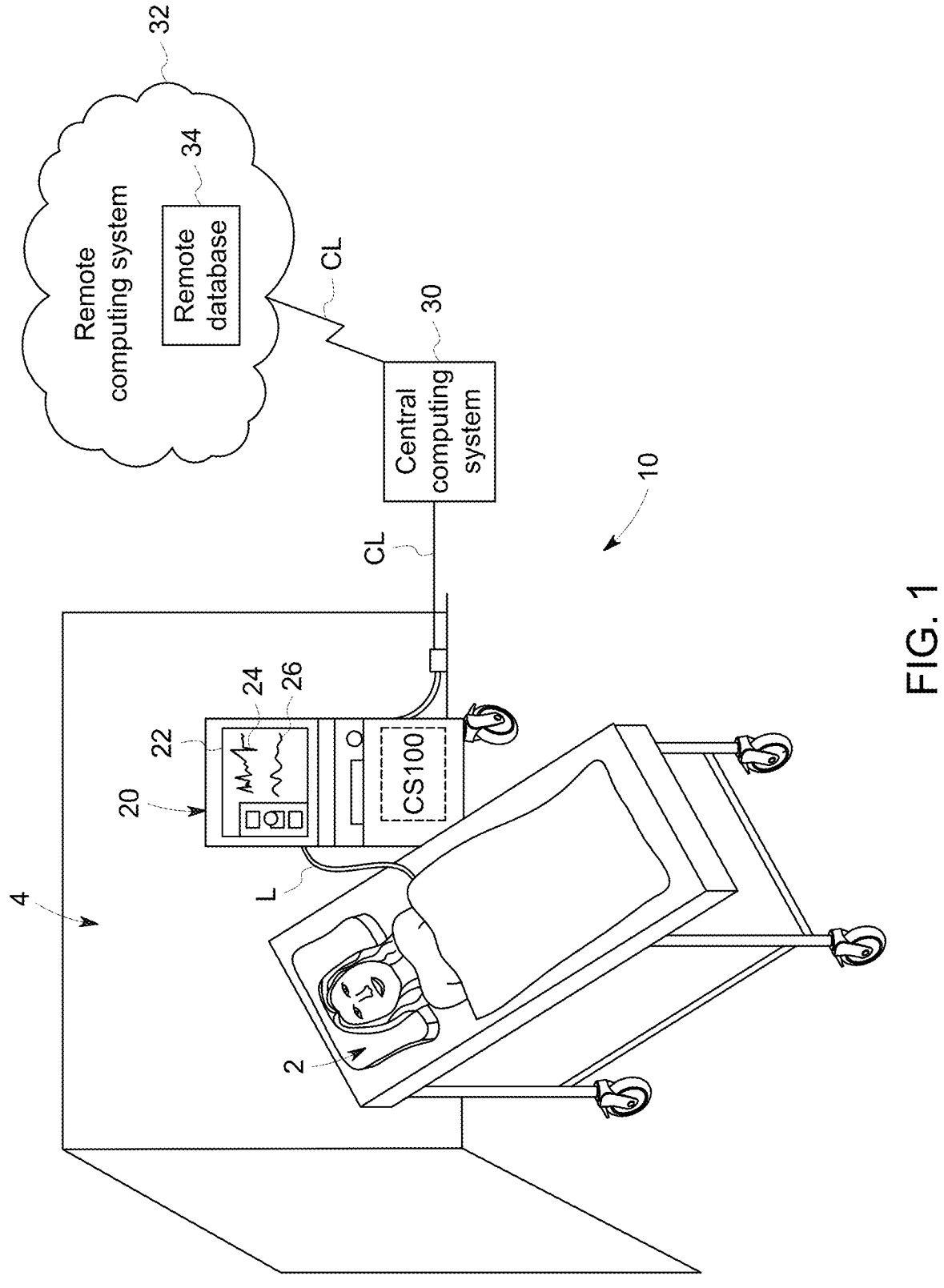
FIG. 1 is perspective view of a medical device according to the present disclosure in-use for monitoring a patient.

The present inventors have recognized that the visualization of the cardiac information produced by electrocardiography devices (ECGs) is limited for devices presently known in the art. Moreover, it is highly complicated to make a diagnosis and conclude an anatomical correlation to the heart using the cardiac information in the manner historically presented, particularly for less experienced practitioners. For the sake of simplicity, the present disclosure will generally refer to analysis of the ST portion of cardiac information, though it should be recognized that the concepts disclosed herein are not limited in this manner.

The evaluation of ST segment data on patients presenting with potential cardiac events is critical in confirming the diagnosis, and also in determining the appropriate therapeutic measure for a patient for STMI (ST-elevated myocardial infarction) versus NSTMI (non-ST-elevated myocardial infarction) episodes. ST segment data is further critical as a tool for assessing reperfusion or revascularization in the case of STMI. In this manner, ST segment analysis is typically a top priority and need for a bedside caregiver (e.g., emergency medicine doctor) in quickly and accurately triaging the case and engaging secondary care specialists (e.g., cardiologists) for performing procedures, conducting further analysis, and/or monitoring the patient. Additional challenges arise in the context of use within emerging markets, rural areas, and/or facilities with resource constraints, whereby having a combination of high-end patient monitoring devices with advanced diagnostic algorithm capabilities available, and also highly trained clinicians, is less likely.

The present inventors have identified an unmet need for a medical device providing a simplified, dedicated, and more meaningful representation of the ST segment data, and particularly in providing an anatomical correlation of perfusion areas to aid in bedside ST analysis and reperfusion or revascularization assessment. Furthermore, the region of a myocardial infarction (MI) is highly important in predicting the clinical severity and extension of the MI. For example, an anterior wall MI is generally associated with more severe coronary artery disease than an interior wall MI. In certain examples, the caregiver may elect to review ST segment data with anatomical correlation of perfusion areas over a specific period. Additionally, the present inventors have recognized a need for a medical device providing multiple different modes of presentation of this ST information to gain further insight into the proper diagnosis, and also address different styles and abilities for making this diagnosis. In certain examples, a given medical device may only have a subset of these different modes of presentation available to the user (including only a single mode of presentation), may be upgradeable to include further modes, and/or may offer different payment options for using additional modes, for example. In short, the presently disclosed devices and methods provide the caregiver with the power and flexibility to choose a presentation mode most comfortable and readable for a given situation.

While the present disclosure principally references the ST segment of ECG data, it should be recognized that the medical devices and methods for presenting cardiac information disclosed herein are also applicable for other segments of ECG data. This may include data corresponding to the PR segment, the TP segment, the J point, and/or the QRS segment (also referred to in the art as the QRS complex), for example.

FIG. 1 shows a patient 2 positioned on a bed within a room 4 of a medical facility, such as a hospital or medical clinic. The patient 2 is operatively connected to a medical device 20, such as a GE Healthcare's® B1×5 M/P patient monitor, using leads L in a customary manner. The leads L is typically used herein to refer to all of the multiple individual leads therein, whereby the individual leads can also be referred to within sets of leads within the leads L (e.g., a first, second, and third set of individual leads that together comprise the leads L). In a typical case of an ECG as the medical device 20, twelve leads L are placed on the patient 2, though other numbers of leads L are also contemplated. The medical device 20 receives the outputs from the leads L and generates cardiac information 27 that can be presented to the caregiver for monitoring and diagnosis (e.g., including voltages from the leads L and differences therebetween).

The medical device 20 includes a computing system CS100, which controls operation of the medical device 20. Additional information regarding the computing system CS100 is provided below. The medical device 20 shown here further includes a display device 22 that serves as a graphical user interface (for example, a touch-screen GUI 24). Waveforms 26 are produced on the display device 22 for the different physiological parameters being monitored. Additional information may also be provided on the display device 22, which also enables a user to configure the medical device 20 in a customary manner, and also in the manner discussed further below in accordance with the present disclosure.

The medical device 20 is part of a greater system 10, which includes a central computing system 30 operatively connected to the medical device 20 via a communication link CL in a manner presently known in the art. In the configuration shown, the central computing system 30 is further connected to a remote computing system 32, which may be accessible as a cloud computing device over the internet, for example. The remote computing system 32 of the present system 10 further includes, either directly or indirectly, a remote database 34, as discussed further below.

It should be recognized that the central computing system 30 and the remote computing system 32 may be incorporated into a single device, whether positioned locally (e.g., within a hospital) or remotely. Likewise, it should be recognized that the elements of the central computing system 30, the remote computing system 32, and the medical device 20 may be further combined or subdivided from the examples discussed herein while preserving the same function.

Figure 2:
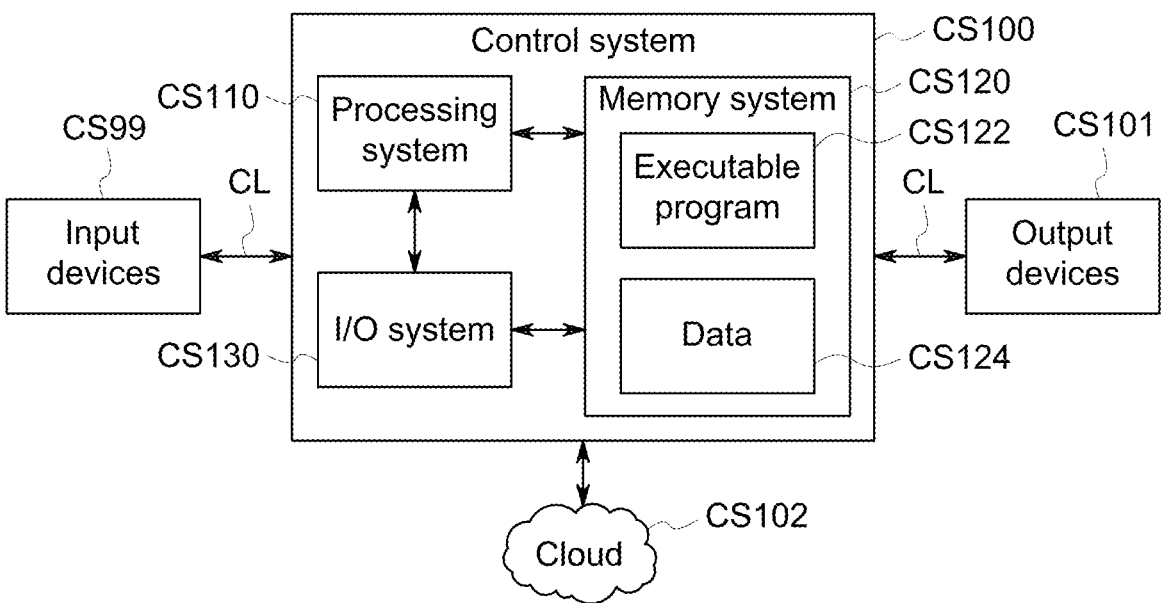
FIG. 2 is a schematic view of an example of a control system such as may be incorporated within the medical device, remote database, and/or external devices.

FIG. 2 depicts an example of a control system CS100 such as may be incorporated within the medical device 20 of FIG. 1. The same of similar structure may also or alternatively be provided as part of the central computing system 30, and/or remote computing system 32 (e.g., with the remote database 34 in certain examples being the memory system CS120). Certain aspects of the present disclosure are described or depicted as functional and/or logical block components or processing steps, which may be performed by any number of hardware, software, and/or firmware components configured to perform the specified functions. For example, certain embodiments employ integrated circuit components, such as memory elements, digital signal processing elements, logic elements, look-up tables, or the like, configured to carry out a variety of functions under the control of one or more processors or other control devices. The connections between functional and logical block components are merely examples, which may be direct or indirect, and may follow alternate pathways.

In certain examples, the control system CS100 communicates with each of the one or more components of the system 10 via a communication link CL, which can be any wired or wireless link. The control module CS100 is capable of receiving information and/or controlling one or more operational characteristics of the system 10 and its various sub-systems by sending and receiving control signals via the communication links CL. In one example, the communication link CL is a controller area network (CAN) bus; however, other types of links could be used. It will be recognized that the extent of connections and the communication links CL may in fact be one or more shared connections, or links, among some or all of the components in the system 10. Moreover, the communication link CL lines are meant only to demonstrate that the various control elements are capable of communicating with one another, and do not represent actual wiring connections between the various elements, nor do they represent the only paths of communication between the elements. Additionally, the system 10 may incorporate various types of communication devices and systems, and thus the illustrated communication links CL may in fact represent various different types of wireless and/or wired data communication systems.

The control system CS100 may be a computing system that includes a processing system CS110, memory system CS120, and input/output (I/O) system CS130 for communicating with other devices, such as input devices CS99 (e.g., sensors and other devices connected to the medical device 20) and output devices CS101 (e.g., the central computing system 30, remote computing system 32, an Electronic Medical Record, and/or other external devices (e.g., smart phones or tablets), which may also or alternatively be stored in a cloud 102. The processing system CS 110 loads and executes an executable program CS122 from the memory system CS120, accesses data CS124 stored within the memory system CS120, and directs the system 10 to operate as described in further detail below.

The processing system CS 110 may be implemented as a single microprocessor or other circuitry, or be distributed across multiple processing devices or sub-systems that cooperate to execute the executable program CS122 from the memory system CS120. Non-limiting examples of the processing system include general purpose central processing units, application specific processors, and logic devices.

The memory system CS120 may comprise any storage media readable by the processing system CS110 and capable of storing the executable program CS122 and/or data CS124. The memory system CS120 may be implemented as a single storage device, or be distributed across multiple storage devices or sub-systems that cooperate to store computer readable instructions, data structures, program modules, or other data. The memory system CS120 may include volatile and/or non-volatile systems, and may include removable and/or non-removable media implemented in any method or technology for storage of information. The storage media may include non-transitory and/or transitory storage media, including random access memory, read only memory, magnetic discs, optical discs, flash memory, virtual memory, and non-virtual memory, magnetic storage devices, or any other medium which can be used to store information and be accessed by an instruction execution system, for example.

Figure 3:
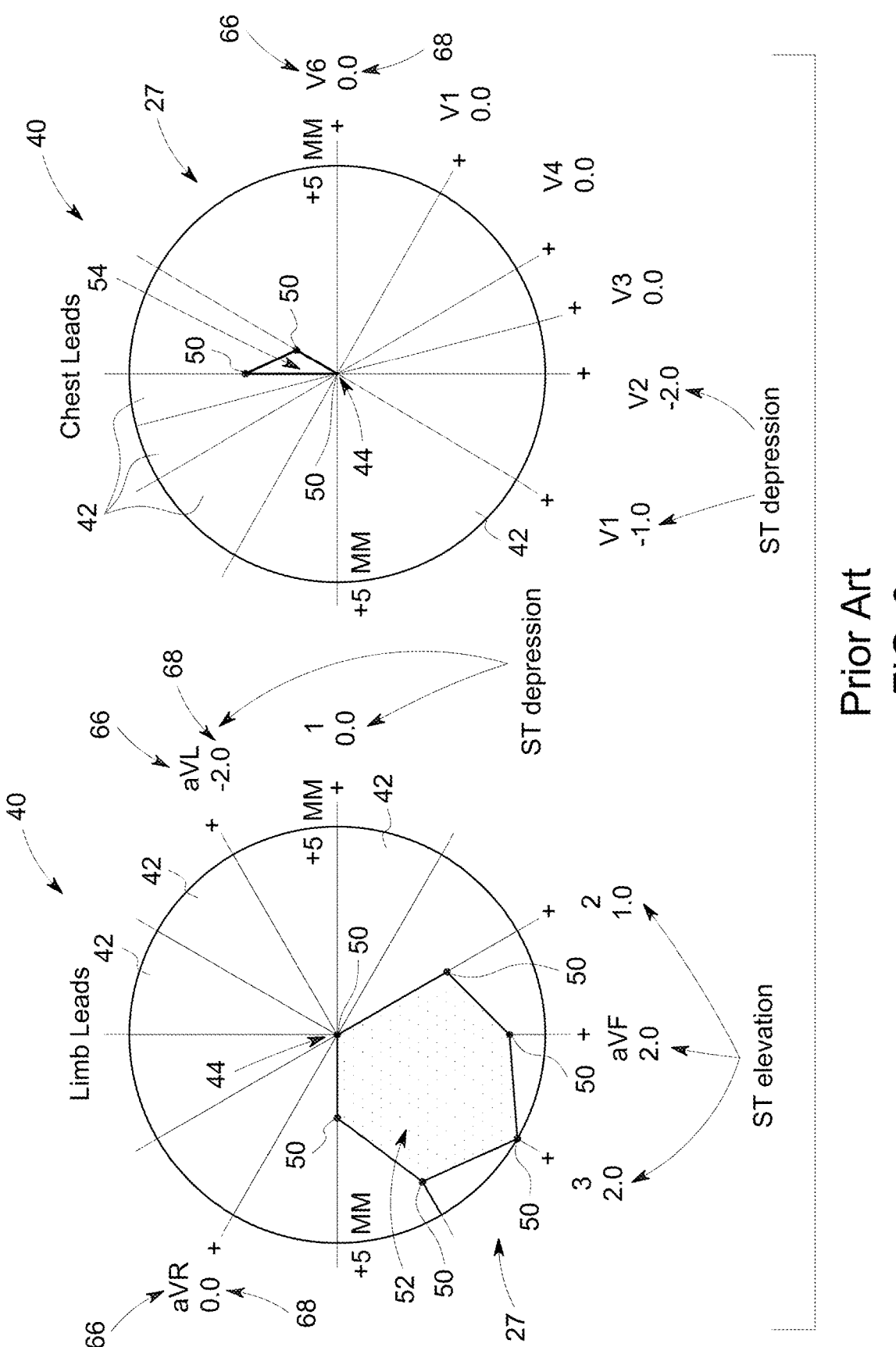
FIG. 3 depicts a presentation of cardiac information within a radar chart as known in the art.

FIG. 3 shows the presentation of cardiac information 27, and specifically information from the ST segment of an ECG, using medical devices and methods presently known in the art. FIG. 3 includes two radar charts 40 for the individual leads within the leads L corresponding to the "limb leads" as known in the art (shown on left), and to the "chest leads" as known in the art (shown on right). Each of the radar charts 40 is circular, emanating outwardly from a center 44 and divided into different sectors 42. Data points 50 collected from the leads L are plotted on the corresponding radar chart 40 at the respective value 68 (e.g., voltage in mV). Each data point 50 is also labeled with its conventional name 66 (e.g., aVL) and value 68 (e.g., −2.0 mV) in numeric form for ease of review.

The data points 50 are further categorized as corresponding to sets, a first set 52 for those among the limb leads and a second set 54 for those among the chest leads. The data points 50 within each set are further connected by lines and filled in to show shapes, again for ease of review. In the example of FIG. 3, some of the data points 50 in the radar charts 40 would be traditionally characterized by a caregiver as demonstrating ST elevation, and others as demonstrating ST depression, as labeled. However, the present inventors have found that this basic presentation of the cardiac information is limited in diagnostic capability. For example, medical devices and methods presently known in the art lack additional insights such as further groupings of individual leads, historical changes to data points, and a clear and direct presentation of the anatomical correlation to the data being shown.

Figure 4:
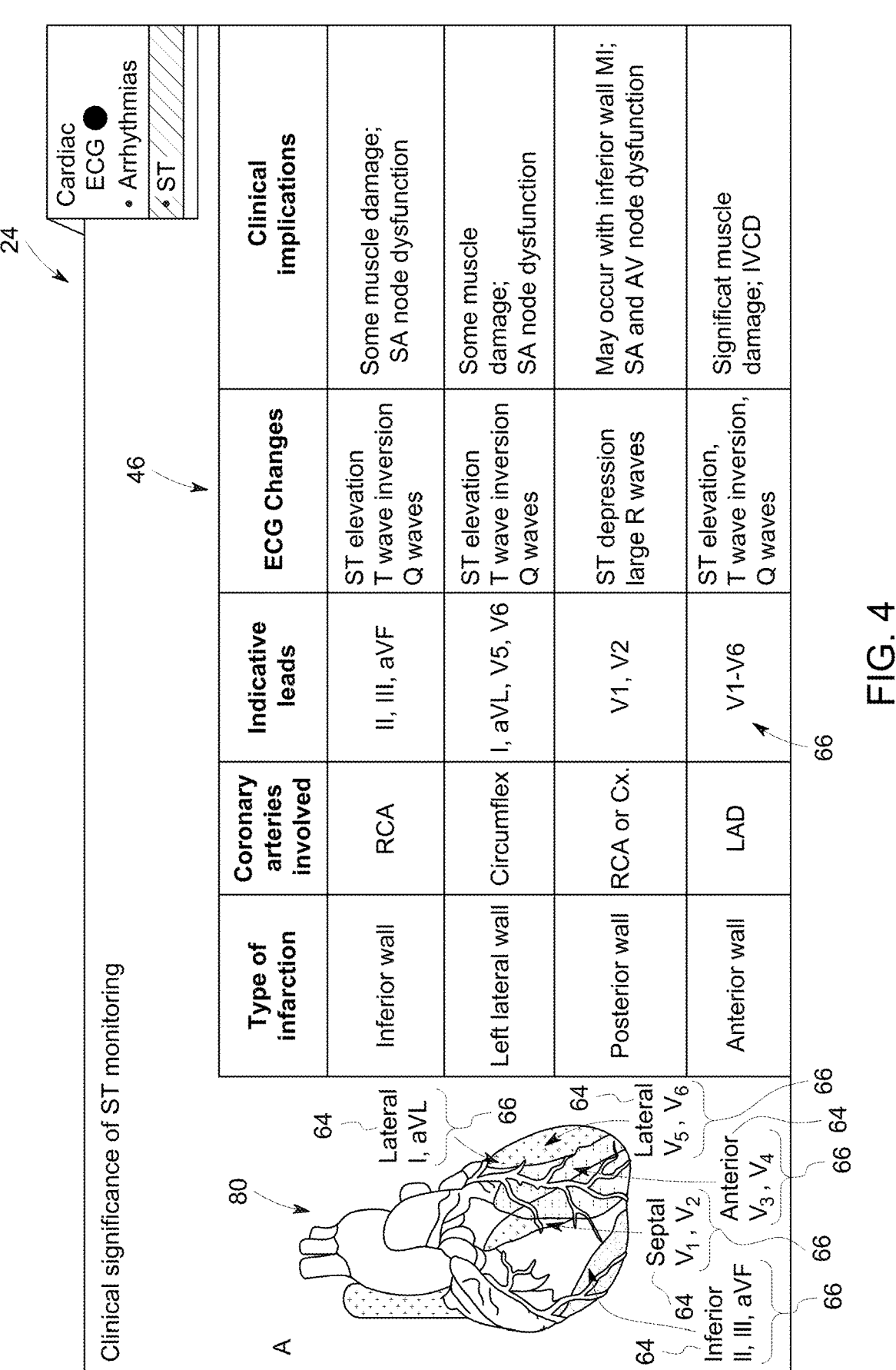
FIG. 4 shows a table with the clinical significance of ST monitoring for ECG data corresponding region of the heart.

FIG. 4 is a table 46 of the clinical significance of ST monitoring for ECG data corresponding region of the heart (Deborah Klein, MSN, RN, ACNS-BC, CCRN, CHFN, FAHA-12 Lead ECG Interpretation training PDF), which may be substantively provided within the GUI 24 of the medical device 20 for reference by the caregiver and/or for training purposes. A heart model 80 is also provided, which includes region names 64 and lead names 66 for correlating the regions of the heart with cardiac information 27 received by the leads L. As discussed above, the medical devices and methods presently known in the art require the caregiver to review data such as is provided in the radar charts 40 of FIG. 3, then diagnose the likely region of the heart affected by referencing the table 46 of FIG. 4.

Figure 5:
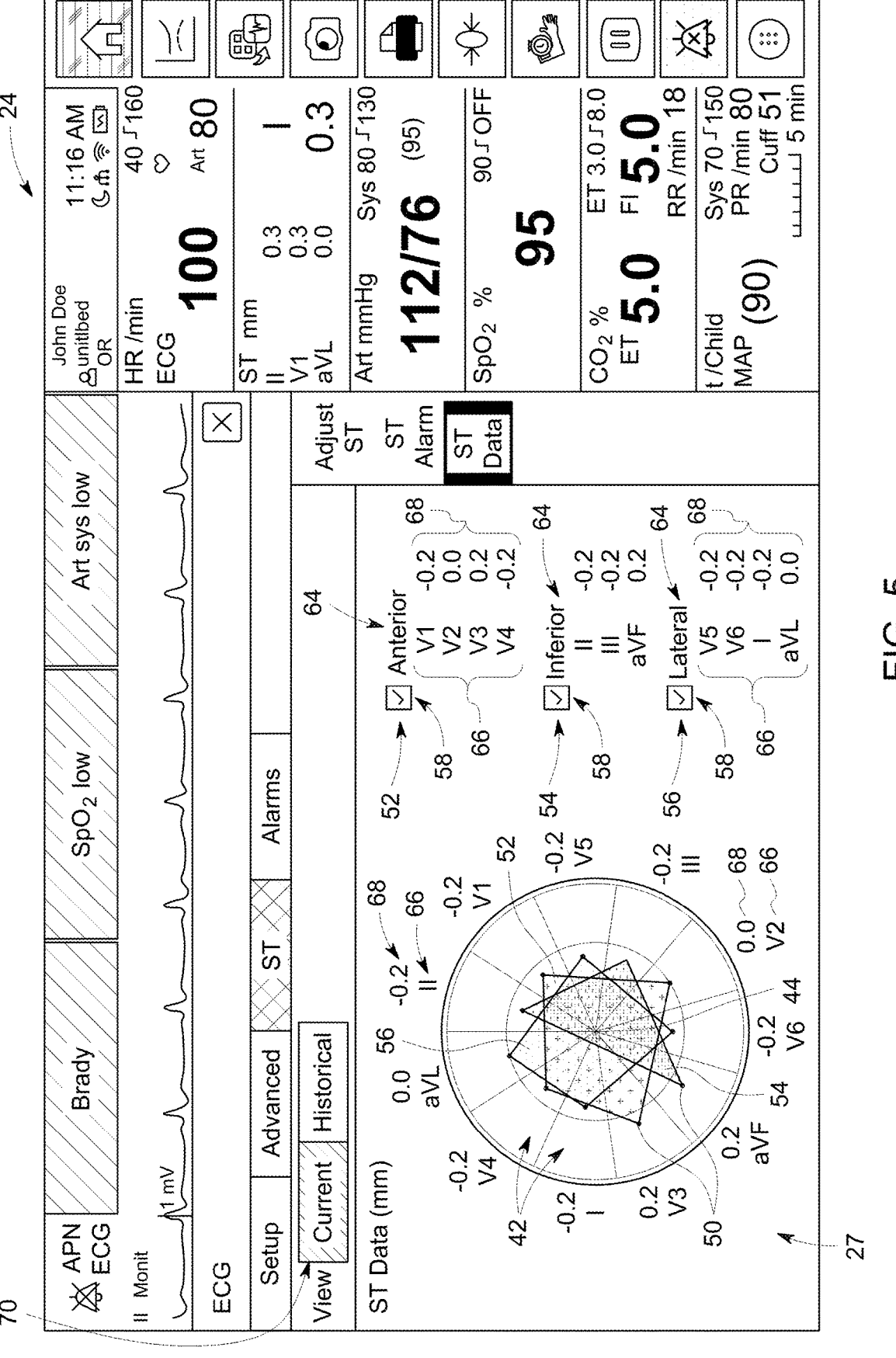
FIG. 5 is a screenshot of a medical device presenting cardiac information in a first manner according to the present disclosure.

FIG. 5 shows a screenshot of a medical device 20 presenting cardiac information 27 in a first manner according to the present disclosure, here showing a current menu 70 for displaying current data being received from the leads L (see FIG. 1). FIG. 9 shows one example of a method 200 for presenting cardiac information 27 according to the present disclosure, which may be used to generate the screen of FIG. 5, and thus reference is now made to both FIGS. 5 and 9 together.

Step 202 provides for receiving the cardiac information collected via the leads L, which is performed by the medical device 20 in a customary manner. Step 204 provides for detecting an ST segment within the cardiac information, which again may be in a customary manner. A radar chart 40 is then produced on the GUI 24 and divided into sectors 42 in step 206. In the example shown, the sectors 42 are equally sized and shaped. Unlike methods of presentation currently known in the art, the method 200 includes separating the leads L into a first set 52 of individual leads within the leads L, and a second set 54 of individual leads within the leads L, which are plotted in step 208 in the radar chart 40 so as to be visually distinguishable from each other.

Specifically, data from each of the individual leads are plotted as data points 50, then connected with lines and shaded, colored, and/or otherwise provided with visually distinguishable features by set (e.g., first set 52 versus second set 54). In one example, the first set 52 forms a shape filled in as a green color and the second set 54 forms a shape filled in as a red color, and/or is shown darker than the first set 52. The cardiac information 27 shown on the screen further includes the lead names 66 and lead values 68 from each of the individual leads, in this example clustered by region and listed under the region name 64 for ease of review.

For example, all of the individual leads (e.g., V1, V2, V3, V4) within the "anterior" region are shown together, along with the corresponding values 68 at that moment in time. The presentation is further configurable by selection of check boxes 58, which select whether data points 50 and the corresponding shape, colors, and the like are shown in the radar chart 40. This allows the caregiver to isolate regions of concern for ease of review. Other regions may also be selectable in addition or in the alternative to what is shown in FIG. 5, such as "Septal" as a region name 64, which when selected includes data corresponding to individual leads V1 and V2. It should be recognized that this data corresponding to the septal region may be presented in addition to what is shown (e.g., as a fourth lead name 64 selected), including when anterior is selected (despite having two individual leads, V1 and V2, in common). In certain examples, the coloration and/or other indicator is selected to not only distinguish between the sets of individual leads, but also to highlight which set contains individual leads having lead values 68 exceeding limits (e.g., showing a first set 52 in red if the data contained therein is triggering an alarm or suspected to be indicating a problem). Additionally, any lead values 68 found to exceed a threshold stored in the memory system CS120, whether an absolute threshold or a threshold for a value or change in value over time, can cause audible alarms, warning displays on the display device 22 and/or other remote devices (e.g., a tablet or central monitoring station), or further changes to the GUI 24. The medical device 20 may also or alternatively automatically generate and transmit an alert to a caregiver (e.g., a text or email-like message), generate and transmit a request for review by a specialist (e.g., a surgeon), or automatically schedule testing, imaging, surgery, and/or other procedures. In addition or in the alternative, the coloration and/or other indicator may be selected to highlight a non-physiological condition (e.g., showing dark red is a communication error has occurred with one of the individual leads). A message may also be displayed on the display device 22 recommending that the caregiver inspect and/or reposition one or more of the individual leads. Beyond alerts indicating problems (e.g., a medical condition detected within the data, physiological conditions indicating a deterioration of the patient's condition, system errors, and/or communication errors), alerts may be generated and transmitted to indicate that new data is available for viewing (e.g., a radar chart has been updated), or to recommend changes to the data being displayed (e.g., a different duration of data being shown on a single radar chart, such as showing 10 minutes of data rather than 1 hour of data for a more detailed display of individual data points).

In further examples, the medical device 20 may automatically ignore problematic individual leads, and/or modify a preferred default of how the data is presented on the display device 22, based on issues with individual leads and/or lead values 68 of particular interest. For example, if the medical device 20 determines that the lead values 68 are shifting significantly over time (e.g., via comparison to an absolute or relative threshold), the GUI 24 may automatically present the relevant data in a historical menu to highlight this shift for the caregiver. Alarms, display conditions, and/or messages may also or alternatively be presented on the GUI 24, and/or external devices in communication with the medical device 10.

In total, the presentation of FIG. 5 allows the user to visualize the cardiac information 27 from the leads L in a single radar chart 40, yet distinguishable by the region of the heart for improved diagnosis by the caregiver. For example, one can immediately discern which of the regions has corresponding data points 50 farthest from the center 44 of the radar chart 40.

Figure 8:
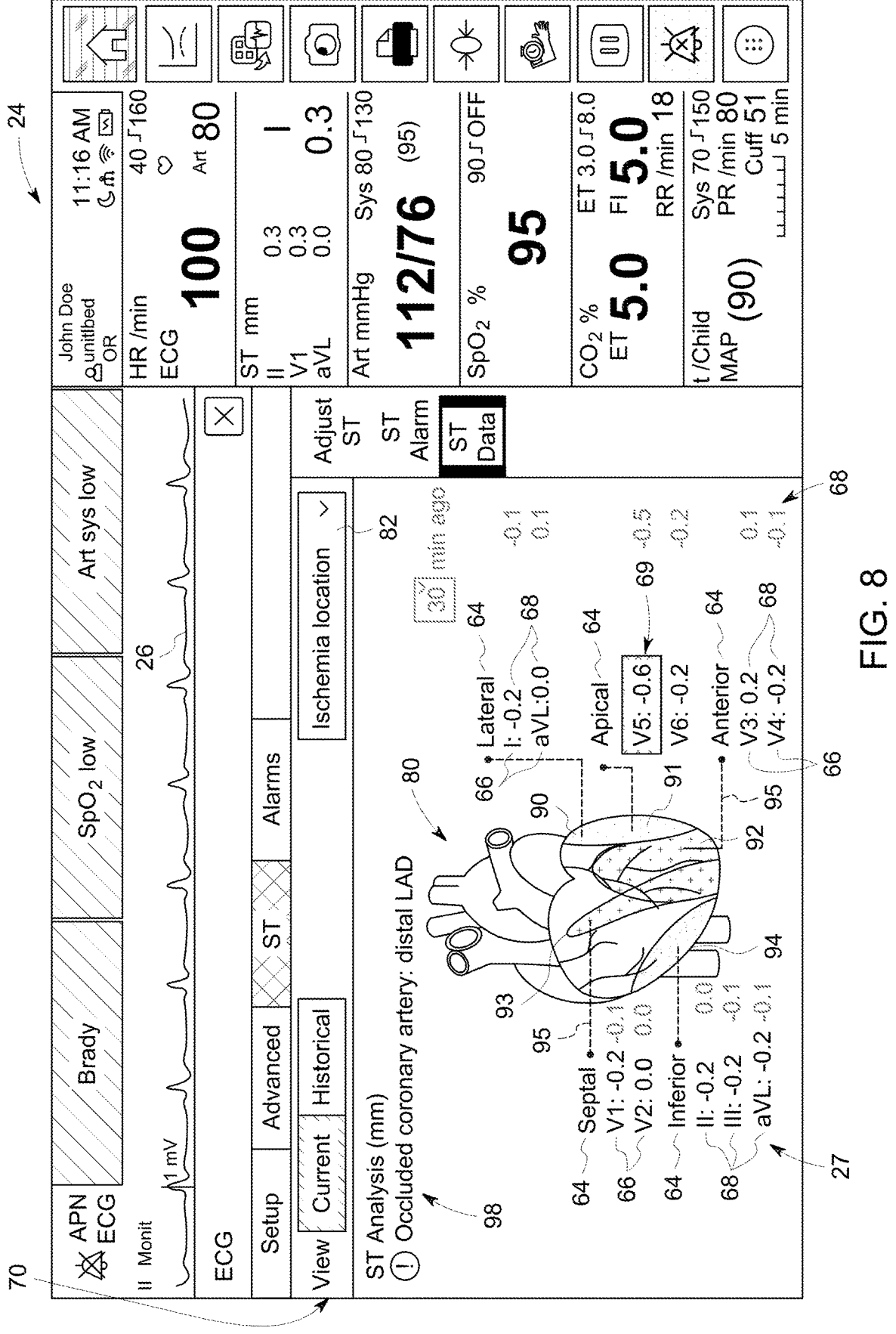
FIG. 8 is a screenshot of a medical device presenting cardiac information in a fourth manner according to the present disclosure.

The present inventors have recognized that in certain situations, a further alternative presentation of the cardiac information in a given instance (also as a "current" menu) would be highly advantageous for the diagnosis and treatment of a patient, including to confirm success of an intervention or to provide aid for a less experienced practitioner. FIG. 8 shows an example of a presentation in this manner, which includes a heart model 80 displayed on the screen that depicts the different regions of interest for the heart: lateral 90, apical 91, anterior 92, septal 93, inferior 94, along with other key landmarks (vessels, walls, and the like). Cardiac information 27 is provided in conjunction with the heart model 80, for example with lines 95 connecting the data to the corresponding region of the heart.

The cardiac information 27 again includes the lead names 66 and lead values 68 corresponding thereto, which are clustered by region name 64 for ease of correlating to the heart model 80. This allows the caregiver to review the lead values 68 and quickly discern which region of the heart is at issue, offering a highly visual presentation that bypasses the data analysis and high-level analysis required by presently known methods. In certain examples, the regions of the heart corresponding to cardiac information that is outside of threshold values may be shown in a different manner, for example coloring the region of interest in red while the remainder of the heart is shown in another color. In other examples, each region of the heart is generally shown in a different color or pattern to help distinguish therebetween. In these cases, the problematic region may still be further distinguished, for example by being shown darker, by flashing on the GUI 24, outlined, or otherwise visually altered. The underly lead value 68 of concern may also or alternatively be highlighted via a box 69 or other mechanism so as to bring the caregiver's attention to the issue. In certain examples, a predicted diagnosis 98 is also displayed when one or more of the lead values 68 indicates a potential problem, providing a suggestion to the caregiver for further investigation or diagnosis.

The example of FIG. 8 further additional lead values 68 in light text, which show additional historical data that can be presented when selecting the "historical" menu rather than the current menu 70. In addition or in the alternative, the heart model 80 when viewed in the historical menu may be colored, shaded, and/or the like based on the amount of change over time. For example, regions that have changed the most over time may be colored in a dark color, with unchanged regions shown in light colors. In other examples, regions with lead values 68 associated with a declining state (e.g., those demonstrating that the patient's condition is worsening) may be shown in red, whereas those stable are shown in white and those improving are shown in green.

Figure 11:
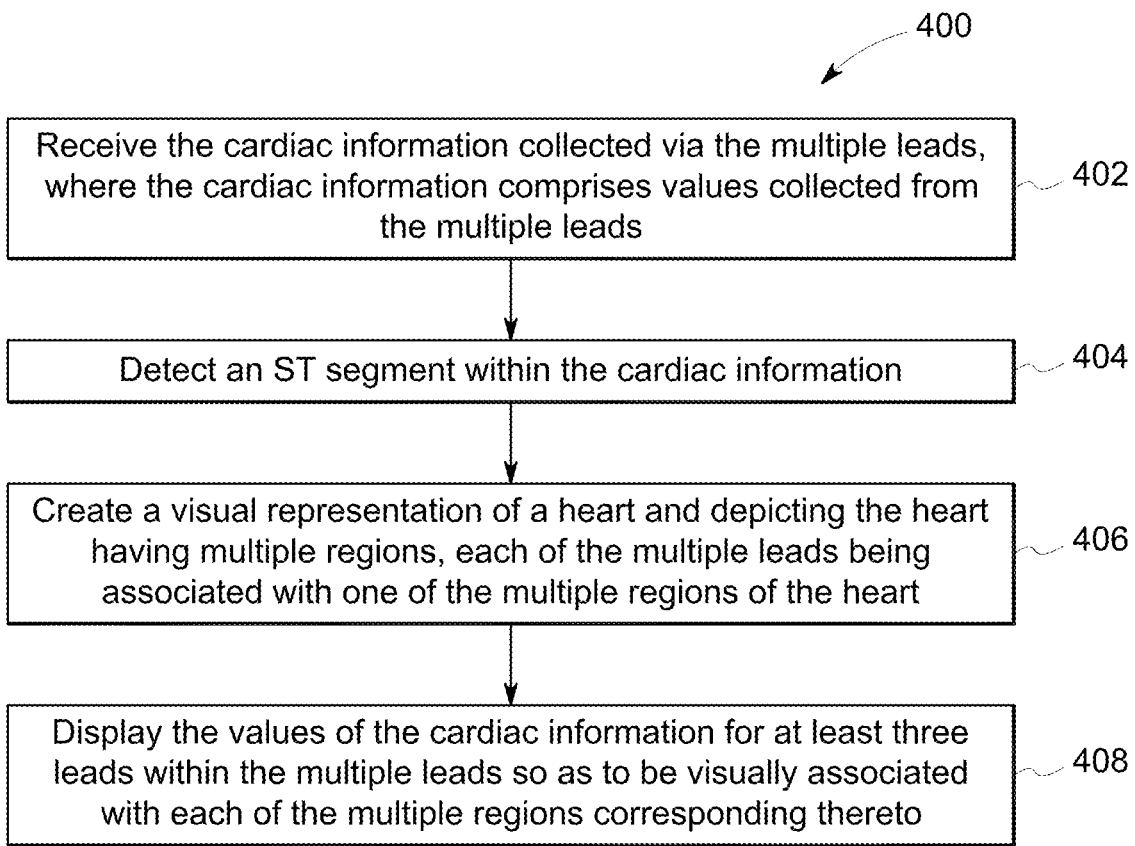
FIG. 11 is a flow chart for a third example of a method for presenting cardiac information according to the present disclosure.

An example method 400 for producing the presentation of FIG. 8 (though not limited thereto) is shown in FIG. 11. Steps 402 and 404 may begin as discussed above for steps 202 and 204 in the method 200 of FIG. 9, for example. Step 406 then provides for creating a visual representation of a heart and depicting the heart as having multiple regions. In step 408, the values of the cardiac information associated with one or more individual leads (in the example of FIG. 11, three individual leads) is displayed so as to be visually associated with the regions associated therewith in the heart depiction.

Figure 6:
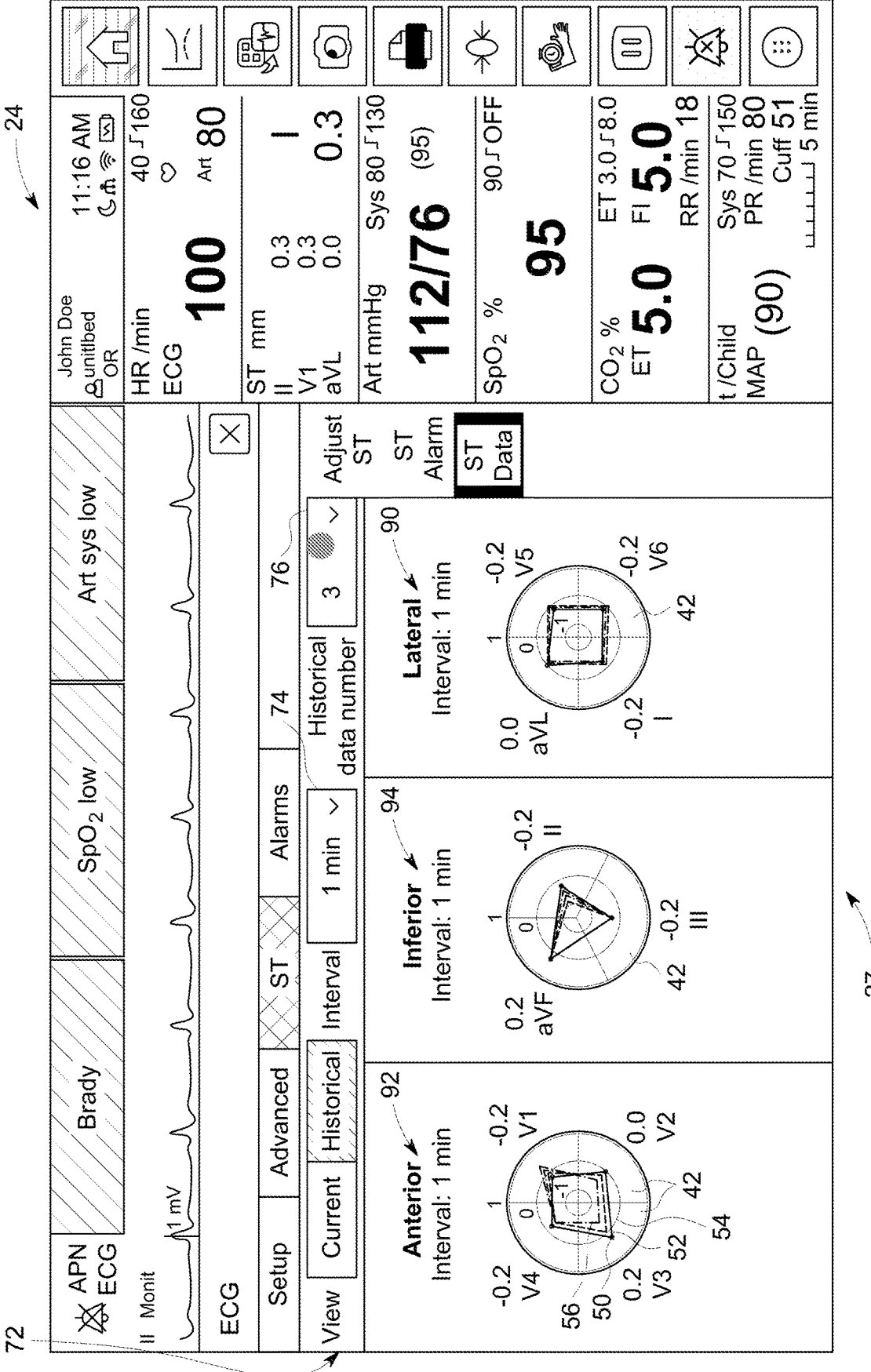
FIG. 6 is a screenshot of a medical device presenting cardiac information in a second manner according to the present disclosure.
Figure 7:
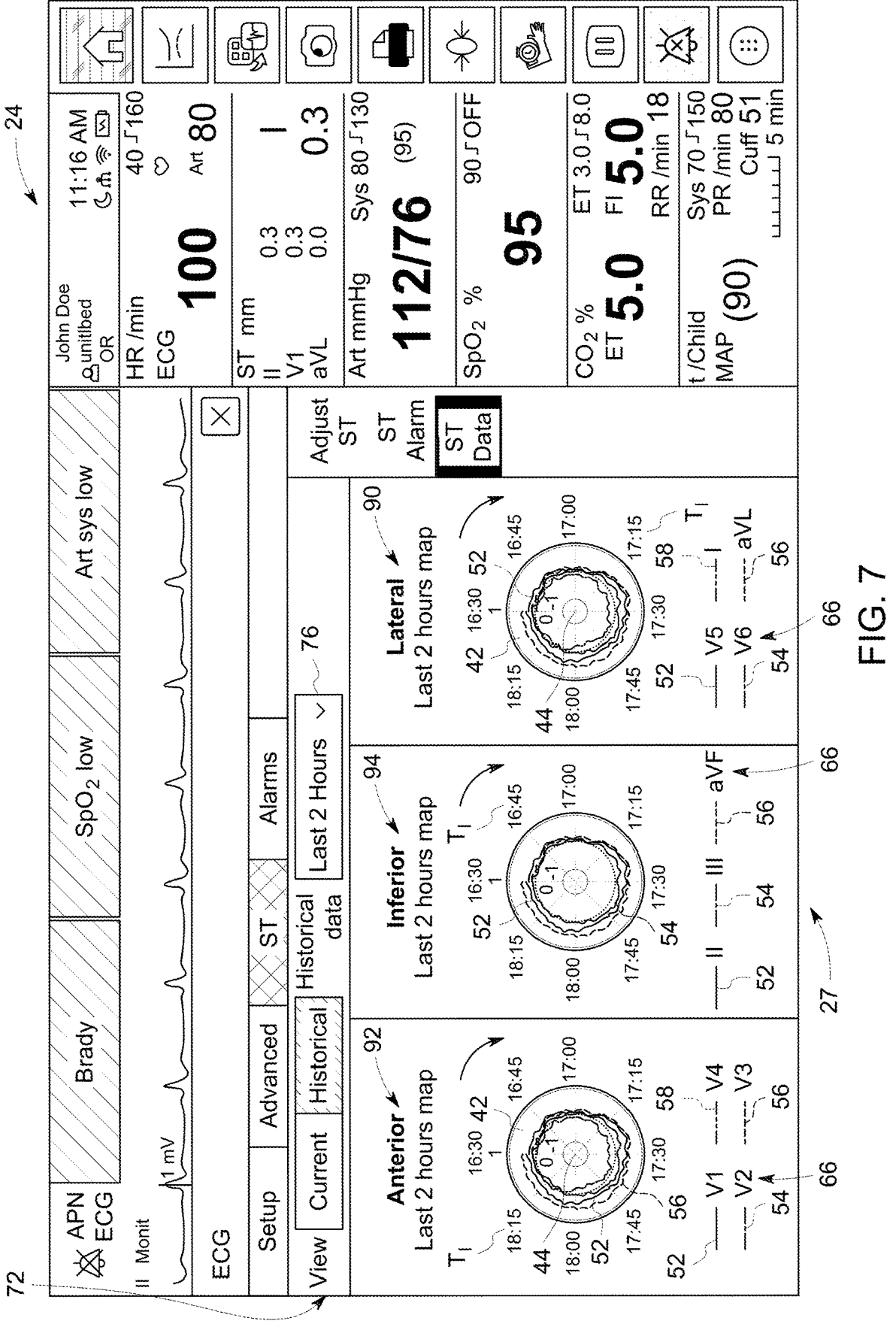
FIG. 7 is a screenshot of a medical device presenting cardiac information in a third manner according to the present disclosure.

The present inventors have further recognized an advantage in providing a medical device 20 configured to also present cardiac information that includes the element of time such that changes can be readily discerned. FIGS. 6 and 7 each show screens in which cardiac information 27 is presented such that the radar chart 40 corresponds to selected regions of the heart, here showing three radar charts 40 corresponding to anterior 92, inferior 94, and lateral 90. In the historic menu 72 shown in FIG. 6, the radar chart 40 for each region of the heart is divided to have one sector 42 for each individual lead associated with that region (e.g., four sectors 42 for the anterior 92 region, which has four individual leads (having names 66 V1, V2, V3, and V4). The name 66 and measured value of each lead over the historical period shown is presented next to the corresponding sector 42 (which in certain example may be presented as an average, weighted average, or moving average, for example).

Data points 50 are plotted for each of the individual leads in the manner previously discussed and connected (and in certain examples, filled in with colors and/or the like) for each given internal of time. In this manner, a first group of data points 50 corresponding to one interval are plotted together as the first set 52, a second group from a second interval are plotted together as the second set 54, and so on. In the example of FIG. 6, the sets of data points 50 are taken at an interval of 1 minute apart (which is selectable by the caregiver via the interval selection 74 and could also include 2 minutes, 5 minutes, 10 minutes, and other time intervals). The number of sets to display is also selectable by the caregiver, specifically through the historical data number selection 76 (other non-limiting examples being 2, 4, or 5). Therefore, the first set 52 corresponds to data collected within the most recent time interval, the second set 54 collected the interval before the first set 52, and a third set 56 collected the interval before the second set 54. Each of the sets remains distinguishable over the others, as discussed above, such that the caregiver can quickly discern changes over time.

Therefore, in contrast to the cardiac information 27 presented in FIG. 5, whereby each set of data points 50 corresponds to a region, FIG. 6 shows the entire radar chart for a region and presents each set of data points 50 corresponding to an individual lead within that region (now over time). The sets may be distinguishable over each other through the use of different colors and the like, but in this case are shown as unfilled shapes having differing styles of connecting lines between data points 50 (e.g., with more space between data points 50, and/or a lighter or thinner line or data points 50 as the set gets older). As a new interval passes, the former first set 52 becomes the second set 54, the former second set 54 becomes the third set 56, and the newest data becomes the new first set 52, for example.

The example method 300 of FIG. 10 may be used to generate the presentation of FIG. 6, but is not limited in that regard. Steps 302 and 304 may proceed in a similar manner as steps 202 and 204 previously discussed with the method 200 of FIG. 9. In step 306, a radar chart is divided into sectors corresponding to the individual leads of a region of the heart. Steps 308 and 310 then provide for plotting groups of data points corresponding to the individual leads within the region represented by the radar chart, whereby different groups are visually distinguishable from the others in the manner described above.

FIG. 7 shows a further example presentation of cardiac information 27 according to the present disclosure, which again advantageously provides the perspective of time. The presentation of FIG. 7 may be provided via the method 200 of FIG. 9 as described above, but is not limited in that regard. The example shown again provides for three radar charts 40 each associated with a region of the heart (here anterior 92, inferior 94, and lateral 90). In contrast to that of FIG. 6, the sectors 42 of the radar charts 40 are not divided to correspond to individual leads for a given region of the heart, but instead relate to periods of time (selectable by the historical data number selection 76, here two hours). In other words, each radar chart 40 is divided into time intervals (here, eight sectors 42) totaling two hours. Each set of data points 50 now corresponds to a single individual lead, for example V1, V2, V3, and V4, and is plotted within the radar chart 40 as the data comes in. In the example shown, there are multiple data points 50 for a given individual lead within the same sector 42 (e.g., there may be 10 or 15 data points 50 within a 15 minutes interval TI as the sector 42). In this manner, changes over time can be seen by reviewing the data points 50 encircling the center 44 of each radar chart 40 (e.g., with no changes for a given individual lead creating a perfect circle).

Figure 12:
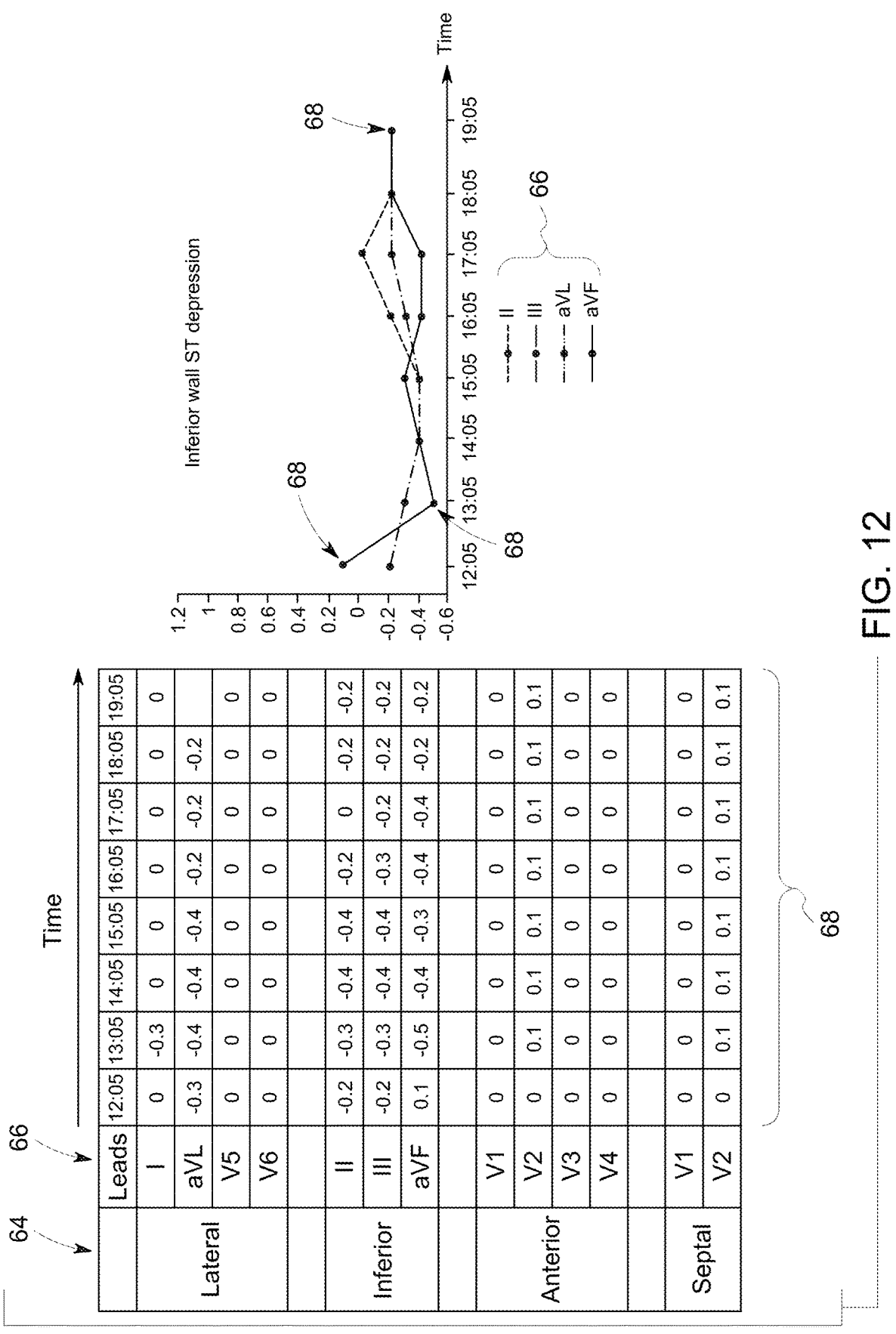
FIG. 12 is a screenshot of a medical device presenting cardiac information in a fifth manner according to the present disclosure.

Each set of data points 50 now remains static rather than being replaced. For example, the first set 52 always represents V1 as the individual lead, the second set 54 as V2, and so on. This presentation allows a caregiver to quickly and simultaneously review not only changes within a given individual lead, but also changes across the individual leads (e.g., relative differences between them). As shown in FIG. 12, a graphical trend may be shown (here as both a data table and chart) to present lead values 68 as a function of lead name 66 and region name 64 over time.

The functional block diagrams, operational sequences, and flow diagrams provided in the Figures are representative of example architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. Certain terms have been used for brevity, clarity, and understanding. No unnecessary limitations are to be inferred therefrom beyond the requirement of the prior art because such terms are used for descriptive purposes only and are intended to be broadly construed. The patentable scope of the invention is defined by the claims and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

What is claimed is:

1. A method for presenting cardiac information originating from multiple leads connected to a patient, the method comprising:

receiving the cardiac information collected via the multiple leads;

detecting a segment within the cardiac information;

creating a radar chart divided into sectors;

plotting data points on the radar chart that correspond to the cardiac information for first and second sets of leads within the multiple leads, wherein the data points corresponding to the first set of leads are shown differently than the data points corresponding to the second set of leads so as to be visually distinguishable from each other, and wherein a first color of the data points for the first set of leads is different than a second color of the data points for the second set of leads;

comparing values of the data points to one or more predetermined thresholds; and visually highlighting which set of leads contains values exceeding the one or more predetermined thresholds in a third color.

2. The method according to claim 1, wherein each of the sectors corresponds to a different one of the multiple leads.

3. The method according to claim 1, wherein the first set of leads is associated with a first region of a heart and the second set of leads is associated with a second region of the heart.

4. The method according to claim 3, wherein the first region and the second region are distinct and are each one of an anterior region, an inferior region, and a lateral region, and wherein the first and second sets of leads each include between three and four of the multiple leads.

5. The method according to claim 1, wherein the first color is the same for all of the data points within the first set of leads.

6. The method according to claim 1, further comprising plotting the data points on the radar chart that correspond to the cardiac information for a third set of leads within the multiple leads, wherein the data points corresponding to the third set of leads are shown differently than the data points corresponding to the first and second sets of leads so as to be visually distinguishable therefrom, further comprising connecting the data points that are adjacent to each other within each of the first set of leads, the second set of leads, and the third set of leads, respectively, to form three overlapping shapes, respectively, wherein each of the three overlapping shapes has a different color.

7. The method according to claim 1, wherein the sectors each correspond to a period of time and the data points are plotted for the first and second sets of leads as a function of the period of time in which each was collected.

8. The method according to claim 7, wherein the first set of leads is a single lead among the multiple leads.

9. The method according to claim 7, further comprising configuring the radar chart such that the period of time for each of the sectors is based on a selection, and further comprising subsequently updating the data points plotted on the radar chart based on the selection.

10. The method according to claim 7, wherein the radar chart corresponds to a first region of the heart, and wherein all of the data points plotted on the radar chart correspond to individual leads among the multiple leads associated with the first region.

11. The method according to claim 7, wherein the data points are plotted continuously and in a circular manner around the radar chart such that older data points among the data points are overwritten by newer data points plotted after the older data points based on the period of time corresponding to the sectors.

12. The method according to claim 7, wherein a first color of the data points for the first set of leads is different than a second color of the data points for the second set of leads.

13. The method according to claim 1, further comprising receiving one of at least a lead-based selection and a time-based selection, wherein receiving the lead-based selection causes the radar chart to be created such that each of the sectors corresponds to one of the multiple leads, and wherein receiving the time-based selection causes the radar chart to be created such that each of the sectors corresponds a period of time, and further comprising subsequently updating the data points plotted on the radar chart based on which of the one of at least the lead-based selection and the time-based selection is received.

14. A method for presenting cardiac information originating from multiple leads connected to a patient, the method comprising:

receiving the cardiac information collected via the multiple leads;

detecting a segment within the cardiac information;

creating a radar chart divided sectors, wherein each of the sectors corresponds to one of the multiple leads;

plotting, within each of the corresponding sectors, a first group of data points corresponding to the cardiac information for at least three leads within the multiple leads;

plotting, within each of the corresponding sectors, a second group of data points corresponding to the cardiac information for the at least three leads within the multiple leads collected subsequently to the first group of data points, wherein the first group of data points are shown differently than the second group of data points so as to be visually distinguishable from each other, and wherein a first color of the first group of data points is different than a second color of the second group of data points;

determining differences between the second group of data points to the first group of data points for the multiple leads, and comparing the differences to a threshold;

generating and transmitting an alert to an external device when at least one of the differences exceeds the threshold;

comparing values of the data points to one or more predetermined thresholds; and visually highlighting which group of data points contains values exceeding the one or more predetermined thresholds in a third color.

15. The method according to claim 14, wherein the second group of data points is shown to be darker than the first set of data points.

16. The method according to claim 15, further comprising plotting an additional group of data points corresponding to the cardiac information for the at least three leads, wherein the first group of data points is removed from the radar chart, the second group of data points becomes the first group of data points, and the additional group of data points become the second group of data points.

17. A method for presenting cardiac information originating from multiple leads connected to a patient, the method comprising:

receiving the cardiac information collected via the multiple leads, wherein the cardiac information comprises values collected from the multiple leads;

detecting a segment within the cardiac information;

creating a visual representation of a heart and depicting the heart having multiple regions, wherein each of the multiple leads is associated with one of the multiple regions of the heart;

presenting the values of the cardiac information for at least three leads within the multiple leads so as to be visually associated with each of the multiple regions corresponding thereto comparing the values to one or more predetermined thresholds and visually highlighting regions of the heart corresponding to values outside of the predetermined thresholds in a different color.

* * * * *